United States Patent [19]

Granier

[11] Patent Number: 4,745,805

[45] Date of Patent: May 24, 1988

[54] PROCESS AND DEVICE FOR THE MEASUREMENT OF THE FLOW OF RAW SAP IN THE STEM OF A PLANT SUCH AS A TREE

[75] Inventor: André F. Granier, Saint-Max, France

[73] Assignee: Institut National de la Recherche Agronomizue, France

[21] Appl. No.: 868,596

[22] Filed: May 30, 1986

[30] Foreign Application Priority Data

May 30, 1985 [FR] France ............... 85 08156

[51] Int. Cl.⁴ .................................. G01F 1/68
[52] U.S. Cl. ........................... 73/204; 47/1 R
[58] Field of Search ................ 73/204; 47/1 R

[56] References Cited

U.S. PATENT DOCUMENTS

| | | | |
|---|---|---|---|
| 1,766,148 | 6/1930 | Sawyer | 73/204 |
| 2,924,972 | 2/1960 | Biermann | 73/204 |
| 3,071,520 | 1/1963 | Smalling | 73/204 X |
| 3,246,515 | 4/1966 | Martino et al. | 73/204 |
| 3,595,079 | 7/1971 | Grahm | 73/204 |
| 4,016,758 | 4/1977 | Taylor | 73/204 |
| 4,135,396 | 1/1979 | Stanne et al. | 73/204 |

OTHER PUBLICATIONS

"Velocity Distribution Patterns in Ascending Swanson Xylem Sap During Transpiration", in I. S. A. Flow-It Measurement & Control, vol. 1, pp. 1425–1430, 1974.

Primary Examiner—Herbert Goldstein
Attorney, Agent, or Firm—Berman, Aisenberg & Platt

[57] ABSTRACT

A process for the measurement of the flow of raw sap in the stem of a tree or other plant, and a device for the embodiment of the process. According to this process, two holes of small diameter are made in the stem, preferably one above the other, and a heating probe equipped with a thermocouple is introduced into the upper hole at the level of the sap-wood, and a non-heating probe is introduced into the lower hole. Comparison of the temperature allows a flow index K to be obtained which gives the value and which is related to the flow u by a law of type $K = A\, u\, \exp.\, B$, where A and B are constants.

5 Claims, 3 Drawing Sheets

• Pseudotsuga menziesli
○ Pinus nigra
+ Quercus pedunculata

4,745,805

PROCESS AND DEVICE FOR THE MEASUREMENT OF THE FLOW OF RAW SAP IN THE STEM OF A PLANT SUCH AS A TREE

FIELD OF THE INVENTION

The present invention relates to a method and to a device for the measurement of the flow of raw sap in the stem of a tree or other plant.

BACKGROUND OF THE INVENTION

Measurement of transpiration constitutes an essential element in the understanding of the physiology of trees and of the dynamics of water transfer in forest plantations. Within the framework of his research in this particular area, the inventor found himself confronted with the problem of the continuous measurement of the flow of raw sap in the trunks of trees. There currently exist numerous methods for measurement of transpiration flow. Among the best known can be cited the so-called "heat-impulse" method described notably by Swanson R. H. in "An instrument for detecting sap movement in woody plants", Sta. Pap. Rocky Mt. For. Range Exp. Sta. No. 68, 1962, and "Velocity distribution patterns in ascending xylem sap during transpiration" in Flow, its Measurement and Control in Science and Industry, Eds. Rodger and Dowdell, Instrument Society of America, Vol. 1, 1425–30, 1974.

However, none of these methods present the specifications required for allowing low-cost monitoring of transpiration in trees in forest plantations. The heat impulse method in particular has two drawbacks: its punctual character in the trunk and its imprecision under conditions of weak transpiration.

GENERAL DESCRIPTION OF THE INVENTION

The aim of the invention is to provide a method which is reliable and precise even for low rates of sap flow, while using only simple and inexpensive equipment.

The invention provides a process for measurement of changes in the flow of raw sap in the stem of a plant, such as a tree, which comprises steps for insertion, in the sap-wood, of two temperature-monitoring probes (one of which is a heating probe and the other is not), supply of an electrical current of constant intensity to the heating probe and recording of the temperature difference between the two probes, these being placed in the same tree, separated by a distance such that the heat released by the heating probe cannot appreciably affect the non-heating probe. The non-heating probe is preferably placed perceptibly on the same vertical line as the heating probe, underneath it.

The invention also provides a device for the embodiment of the process and comprising a heating circuit stabilized by the heating probe, a thermocouple measuring device the hot and cold junctions of which are placed respectively in the heating and non-heating probes, and means of recording the voltage at the terminals of the temperature-monitoring instrument. In this device, the heating probe comprises a rigid tubular core onto which is wound a heating wire, itself surrounded by a heat distributing tube made of material having a high thermal conductivity, such as aluminum, the winding of the wire and the distributing tube being of a length approximately equal to the thickness of the sap-wood into which the probe must be inserted, and the tubular core containing one of the supply wires of the winding.

DETAILED DESCRIPTION OF THE PREFERRED EMBODIMENT

The invention will now be described in more detail by means of the following embodiment, with reference to the accompanying drawings in which.

Figure 1:
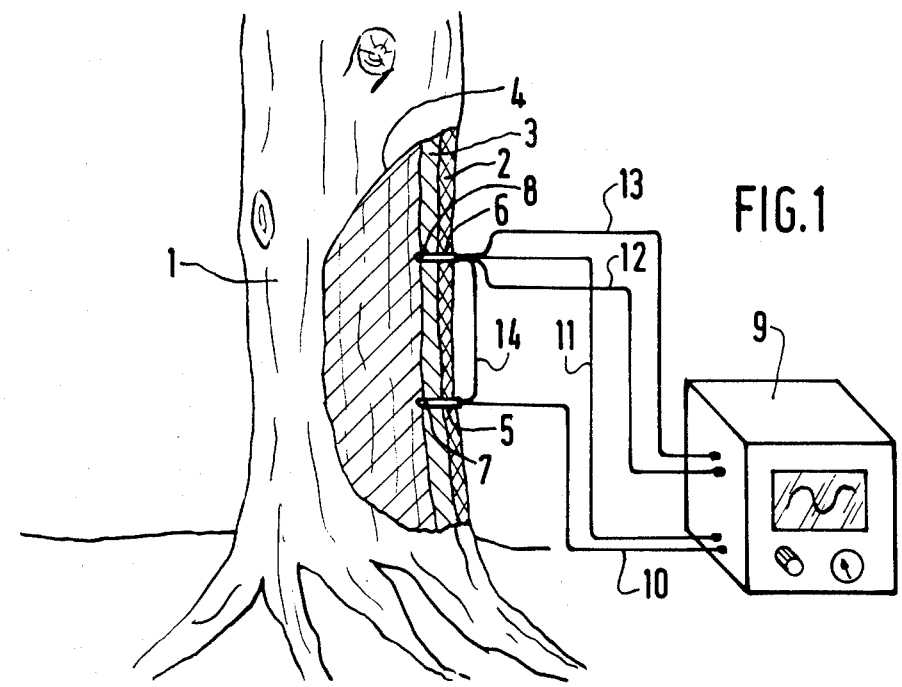
FIG. 1 is a partial diagrammatic cross-section of the device according to the invention.

FIG. 1 shows a tree 1 that one wishes to study. The bark 2, sap-wood 3 and heart 4 of the tree are represented.

For the embodiment of the process, a drill is used to make in the trunk two radial holes 5, 6, having a diameter such that the probes can be introduced thereinto without clearance, friction being nonetheless low enough that they can possibly be recovered. The holes must go through the bark and sap-wood, but it is unnecessary and even inadvisable that they penetrate the heart. In practice, the diameter of the holes is approximately 2 mm, and hole 6, into which the heating probe is introduced is approximately 50 mm above hole 5, which contains the non-heating probe 7. The current supply and recording unit is indicated by 9, and is connected to the probes by temperature-monitoring cables 10, 11 and to the heating probe by supply cables 12, 13. A constantan cable 14 connects the two thermocouple junctions located in the probes.

Figure 2:
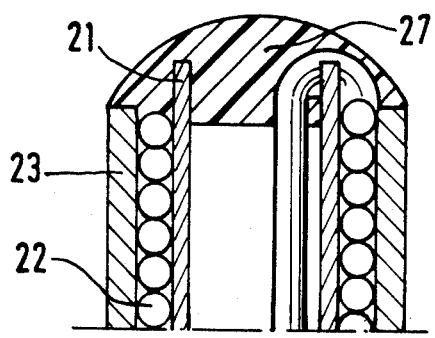
FIG. 2 is a cross-section of the heating probe.
Figure 2:
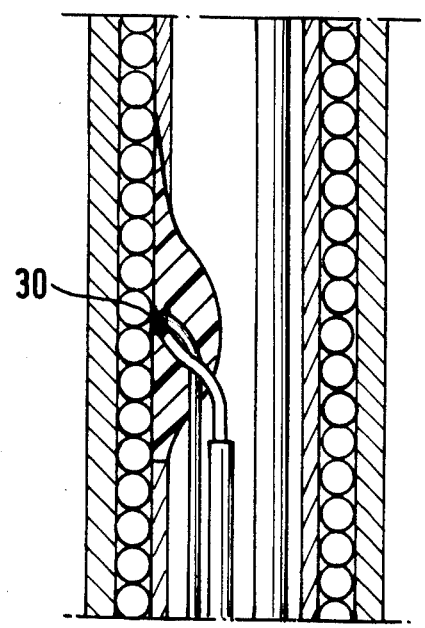
Figure 2:
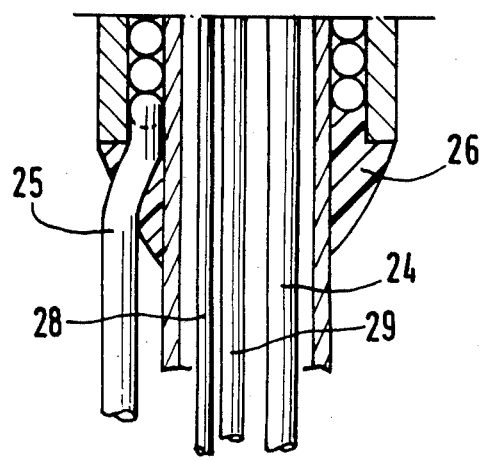

FIG. 2 is a cross-section of the heating probe 8. The core 21 of this probe comprises a thin metal tube, of the type used for injection needles in medical practice. The end of core 21 is surrounded by a winding 22 of approximately 75 turns of constantan heating wire insulated with glass. This winding is held by an aluminum tube 23, which is tightly fitted around the winding and serves at the same time as a temperature distributor. It will be noted that in the example described the length of this tube is 20 mm, for an outer diameter of 2 mm. It seems difficult to miniaturize further without taking risks regarding robustness. The length of 20 mm corresponds to the thickness of the sap-wood 3 of the trees subject to study. One of the supply wires 24 of the winding passes through the inside of core 21, the other 25 is outside. Epoxy adhesive plugs 26, 27 hold the winding and tube 23 in place on the core, one of them also serves to seal the end of the core. The inside of the core also allows passage of two thermocouple wires 28, 29, one of enamelled copper, the other of constantan. Wire 28 is connected by cable 10 to the recorder unit, and wire 29 is connected by cable 14 to an analogous wire of the non-heating probe 7. This non-heating probe is identical to the heating probe, but its wires 24 and 25 are not connected up. A difference in thermal behavior is thus avoided.

The solder 30 between the ends of wires 28, 29 is placed in a small window made in the wall of the core, close to the middle of the winding, and it is immobilized there by a quantity of epoxy adhesive.

In conditions of thermal exchange established between the heating element and the surroundings (wood+sap), and for a constant flow of sap, we shall assume that the heat supply by the Joule effect is equal to the quantity of heat dissipated at the level of the wall of the probe. One therefore has:

$$hS(T-T_b) = Ri^2 \quad (1)$$

with:
- h = coefficient of heat transfer (W·m$^{-2}$·c$^{-1}$),
- S = exchange surface area (m$^2$),
- T = temperature of the cylinder (°C.),
- $T_b$ = temperature of wood material in the absence of heating (°C.),
- R = electrical resistance (Ω),
- i = intensity of the electrical current (A).

It is assumed that the coefficient h is related to sap flow u (m·s$^{-1}$) by an equation of the form:

$$h = h_o(1 + a \cdot u) \quad (2)$$

where $h_o$ is the exchange coefficient when u=0 (zero transpiration), and that it is possible to calculate from (1):

$$h_o = \frac{R \cdot i^2}{S(T_M - T_b)} \quad (3)$$

$T_M$ designates the temperature at zero sap flow (u=0). When u is constant and non-zero, it is given by:

$$u = \frac{1}{a} \frac{T_M - T}{T - T_b} \quad (4)$$

The ratio $$\frac{T_M - T}{T - T_b}$$

is a dimensionless number, which we shall call the flow index K, which is related to u by an equation of the type $K = A \cdot u \exp B$, where A and B are constants.

The probe was tested and calibrated on trunk fragments of diameter ranging between 40 and 50 mm. Water was circulated under pressure in these samples, and simultaneous measurements were made of the flow of water by weighing of the exudate and the signal delivered by the thermal probe. The flow could be modified by adjusting the water pressure. After the measurements, each sample was cut-up to measure the section of the sap-wood at the level of the heating element. Calibration was performed on three different species: Douglas fir, Black pine and Pedunculated oak.

Figure 3:
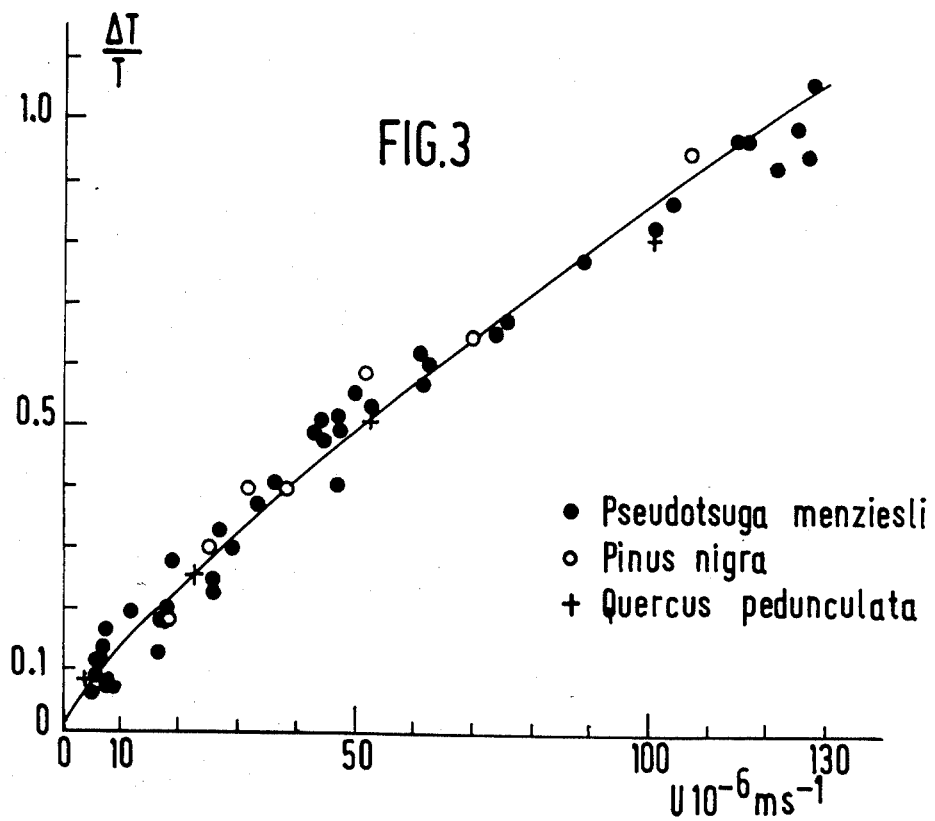
FIG. 3 is a diagram showing the correlation between the flow and changes in temperature.

FIG. 3 shows the results obtained with the abscissa representing water flow per unit surface area u (in m·s$^{-1}$) and the ordinate representing the ratio K. K is calculated from equation (4) knowing for each sample the temperature $T_M$ reached when water flow is zero. It is interesting to note that the relation between K and u is the same for the three species: the coefficient α of equation (4) seems then, under the experimental conditions, to be independent of species. Non-linear fitting leads to the experimental relation:

$$K = 0.0206 \; u^{0.8124} \quad (5)$$

$$r^2 = 0.96$$

$$n = 53 \text{ points}$$

where u is expressed in $10^{-6}$ m·s$^{-1}$.

The intensity of the current in the heating resistance was fixed at a value of 0.140 A, which is a compromise between the sensitivity of the probe (which increases with the intensity applied) and the risk of heating of the reference temperature probe.

Daily recordings of transpiration flow were made with Douglas firs of the national forest of Amance (15 km to the east of Nancy). Trees were chosen in different locations: fully exposed trees, of height 5 m, and trees of a regular plantation 20 years old, of mean height 15 m. Four trees (two in each of the situations) were each equipped with a thermal probe inserted radially into their sap-wood.

Coefficient K depends on the evaluation of $T_M$ (see equation (4) in §1.2). We have assumed that this equilibrium temperature at zero sap flow could be measured at night when the humidity of the air is close to saturation.

Figure 4:
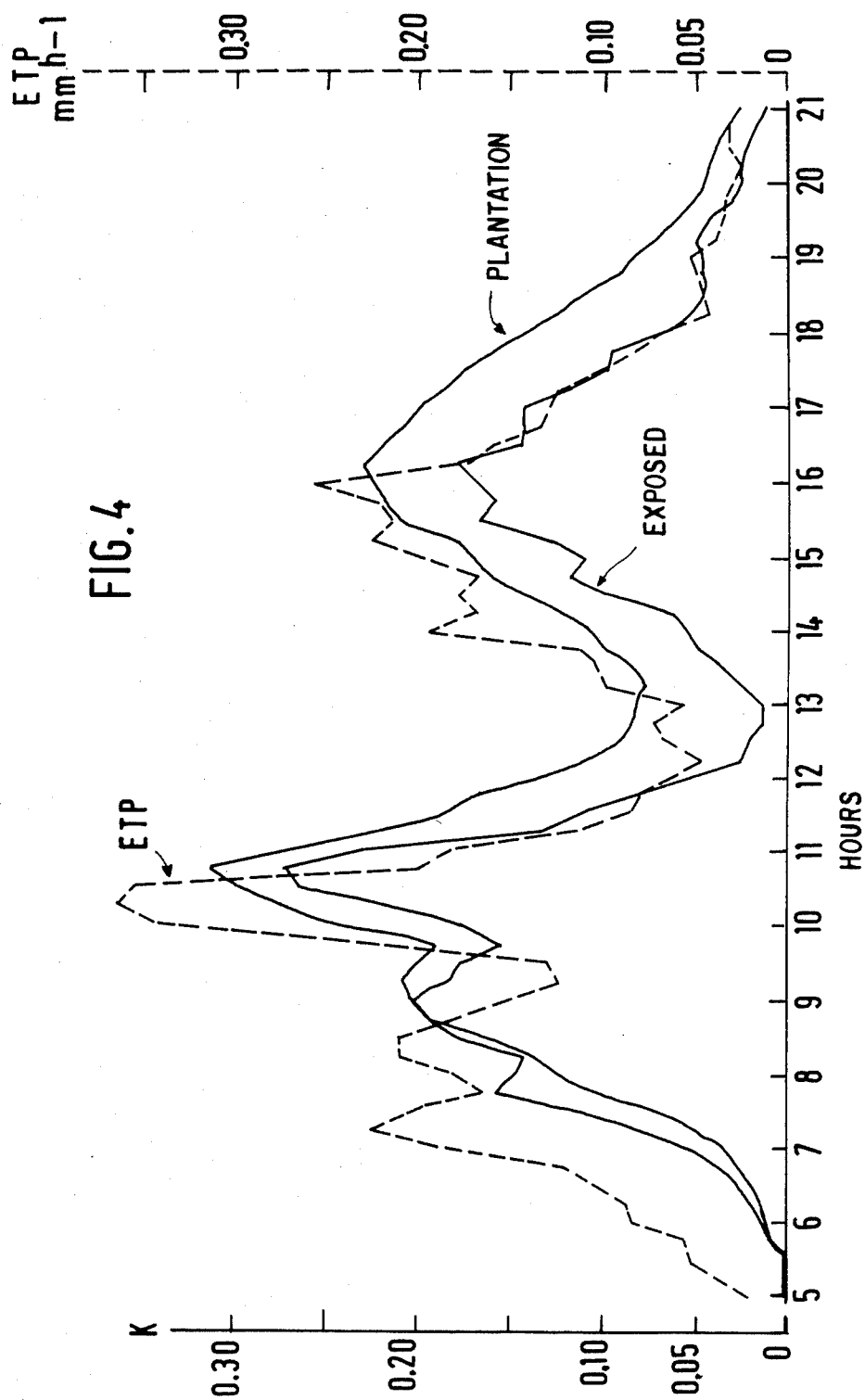
FIG. 4 shows the result of a one-day recording.

FIG. 4 shows the variation in coefficient K during one day, observed for one tree of each treatment, as well as the changes in evapotranspiration potential (E.T.P.) calculated from Penmann's formula. We chose a day with cloudy periods which allowed the response of the probes to be demonstrated. The two trees show a similar trend, in particular in the positions of the maxima and minima. The marked delay of K with respect to E.T.P. in the morning corresponds to a phase of evaporation of dew on the needles. After this phase, the factor K of the two trees follows the variation in E.T.P. It should be noted that the sharp drop in E.T.P. occurring in the middle of the day (cloudy periods) is more marked for the fully exposed tree. The tree of the plantation thus seems to buffer variations in the E.T.P. better. At the end of the day, if K and the E.T.P. decrease at the same time, a delay is seen for the Douglas fir of the plantation.

A large number of days were thus studied as a function of the E.T.P. The coefficient $K_{24}$, equal to the daily mean of K defined according to equation (4), was calculated. It was noted that it is substantially proportional to the E.T.P. as long as the studied tree is permanently well supplied with water; transpiration and therefore the coefficient $K_{24}$ are therefore perceptibly proportional to the E.T.P. However, certain days presenting diurnal rainy episodes fall outside this rule, which is interpreted as follows: the interception of the water by the leafage provokes blockage of transpiration; incident energy is then used to evaporate the intercepted water.

The method that we have described presents a certain number of advantages, which allow reliable results to be obtained on two levels:
  in terms of the water functioning of the tree, by close study of daily variations in sap flow, particularly in periods of water stress;
  in terms of water functioning of forest plantations, knowing that the simple use and low cost of this technique allow quantitative measurement of transpiration and its spatial variability in forests.

The use of this method assumes, when the aim is to calculate the total flow, that the section of the sap-wood at the level of the point of measurement is known. Depending on the type of species and the desired precision, the section of the sap-wood can be estimated thanks to one or several borings with Pressler's auger or by direct measurement after felling of the tree.

I claim:
1. A device for measuring variations in raw sap flow in a sap-wood-containing plant stem which comprises:

a heating temperature probe having a stable heating circuit and a thermocouple measuring device with hot and cold junctions, a non-heating temperature probe having a thermocouple measuring device with hot and cold junctions, a temperature-monitoring instrument having terminals, and means for recording voltage at the terminals;

the heating temperature probe comprising a rigid tubular core surrounded by windings of a heating wire, the windings being surrounded by a heat distributing tube, the composition of which has high thermal conductivity;

the length of the windings and that of the distributing tube being approximately equal to the thickness of the sap wood of the plant stem, and the tubular core containing a supply wire for said windings.

2. A device according to claim 1 wherein the heat distributing tube is an aluminum tube.

3. A device according to claim 1 having a cable which connects the thermocouple junctions of the two probes.

4. A combination of a device according to claim 1 and a sap-wood-containing plant stem wherein both the heating temperature probe and the non-heating temperature probe are in the sap wood and the two probes are displaced from each other by a sufficient distance to preclude heat released by the heating probe from having an appreciable affect on the non-heating probe.

5. A combination according to claim 4 wherein the two probes are vertically displaced from each other, and the heating probe is above the non-heating probe.

* * * * *